United States Patent
Peglion et al.

[11] Patent Number: 6,025,356
[45] Date of Patent: Feb. 15, 2000

[54] DISUBSTITUTED TRANS-3,4,4A,5,6,10B-HEXAHYDRO-2H-NAPHTH[1,2-B]-1,4-OXAZINES

[75] Inventors: Jean-Louis Peglion, Le Vesinet, France; Jean-Christophe Harmange, Andover, Mass.; Mark Millan, Le Pecq; Francoise Lejeune, Saint Cloud, both of France

[73] Assignee: Adir et Compagnie, Courbevoie, France

[21] Appl. No.: 09/144,025

[22] Filed: Aug. 31, 1998

[30] Foreign Application Priority Data

Sep. 1, 1997 [FR] France ................. 97 10852

[51] Int. Cl.[7] ............ A61K 31/535; C07D 498/00
[52] U.S. Cl. ................. 514/229.8; 544/101
[58] Field of Search ............ 544/101; 514/229.8

[56] References Cited

U.S. PATENT DOCUMENTS 4,420,480  12/1983  Jones ................. 424/248.4

*Primary Examiner*—Patricia L. Morris
*Attorney, Agent, or Firm*—The Firm of Gordon W. Hueschen

[57] ABSTRACT

New compounds of formula:

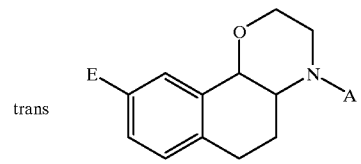

wherein:
A represents alkyl, alkenyl, alkynyl, cycloalkylalkyl or aralkyl, and
E represents:

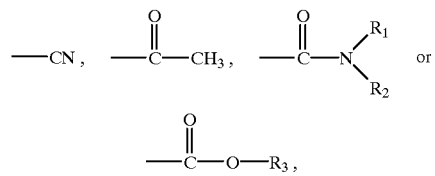

in racemic form or in the form of optical isomers, and the addition salts thereof with pharmaceutically acceptable acids.

Those compounds may be used as medicaments.

9 Claims, No Drawings

DISUBSTITUTED TRANS-3,4,4A,5,6,10B-HEXAHYDRO-2H-NAPHTH[1,2-B]-1,4-OXAZINES

The present invention relates to new disubstituted trans-3,4,4a,5,6,10b-hexahydro-2H-naphth [1,2-b]-1,4-oxazines. It relates more especially to compounds of formula I:

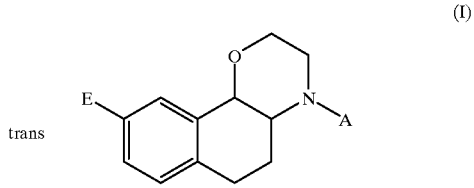

wherein:

A represents: a $(C_1-C_{10})$alkyl, $(C_3-C_{10})$alkenyl or $(C_3-C_{10})$alkynyl radical each of which is straight-chain or branched and optionally substituted by one or more cycloalkyl radicals having from 3 to 8 carbon atoms, or by an aryl radical selected from the radicals phenyl, thienyl and pyridyl each of which is optionally substituted by one or more substituents selected from the halogen atoms, hydroxy radicals, and alkyl and alkoxy radicals each of which has from 1 to 6 carbon atoms and is straight-chain or branched;

E represents:

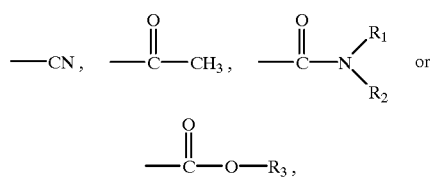

wherein:

$R_1$ and $R_2$, which may be identical or different, each represents a hydrogen atom or has the meaning given for A above, and $R_3$ represents a hydrogen atom or a straight-chain or branched alkyl radical having from 1 to 5 carbon atoms;

in racemic form or in the form of optical isomers, and to the addition salts thereof with a pharmaceutically acceptable acid.

The compounds of formula I act as powerful dopaminergic ligands both in vitro and in vivo Dopaminergic compounds are widely used therapeutically owing to their beneficial effects in psychiatric disorders and, peripherally, in cardiovascular disorders.

Five dopaminergic receptor sub-types ($D_1$ to $D_5$) have now been cloned and characterised. Currently, the great majority of medicaments act on the dopaminergic system by way of their action on the $D_2$ sub-type, either as blockers (or antagonists) or activators (or agonists). Those medicaments have numerous side effects: tardive dyskinesia, hyperprolactinaemia, amenorrhoea in the case of the former, and cardiovascular and motor effects in the case of the latter.

Unlike $D_2$ receptors, the concentration of $D_3$ receptors is very low in the nigrostriated nucleus and in the lactotrophic cells. On the other hand, the concentration of $D_3$ receptors is, like the $D_2$ receptors, very significant in the limbic system. That significant difference in the location of those two sub-types of receptors encourages research into new medicaments that act preferentially on the $D_3$ sub-type and should result in minimising, or in the disappearance of, the side effects typically associated with the $D_2$ sub-type as mentioned above.

Very few products currently claim such a mechanism of action.

The prior art describes tricyclic compounds of aminotetraline (cf. U.S. Pat. No. 5,486,611), but those compounds act preferentially on the serotoninergic system and, more precisely, on the $5HT_{1A}$ receptor sub-type. The compounds of the present invention differ from those products both in terms of their structure and their specificity of action.

Studies carried out in vitro (binding to cloned human $D_2$ and $D_3$ receptors) with the compounds of the present invention demonstrate that those compounds act as preferential ligands of $D_3$, receptors, with less affinity for the $D_2$ receptor.

That characteristic makes the compounds of the present invention especially valuable in view of the low level of side effects exhibited.

Several in vivo tests have confirmed their mechanism of action (recording of the extracellular unitary electrical activity in the ventral tegmentum area of the rat) and the value of their use in the treatment of numerous disorders of the central nervous system.

The compounds of the invention have in particular demonstrated their activity in the ultrasonic vocalisation test in the rat, the forced swimming test, and in the "rotation" test on rats lesioned with 6-OH-DPAT.

The results obtained thus allow the products of the invention to be put forward for the treatment of anxiety, depression, aggressiveness, Parkinson's disease and schizophrenia.

The present invention relates also to a process for the preparation of compounds of formula I which is characterised in that:

a trans compound of formula II:

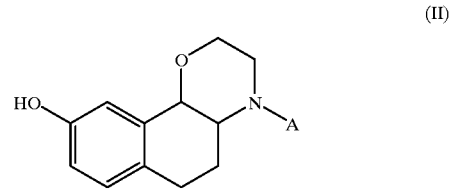

wherein A is as defined hereinbefore, is reacted with triflic anhydride in the presence of pyridine to obtain a trans compound of formula III:

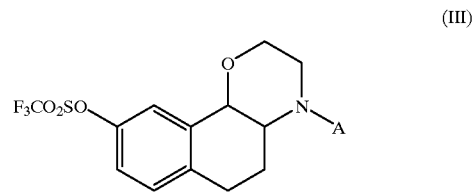

wherein A is as defined hereinbefore, and that compound is reacted:

either with zinc cyanide and tetrakis(triphenylphosphine) palladium(0) in dimethylformamide at elevated temperature to obtain a trans compound of formula Ia:

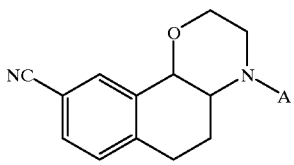

(Ia)

wherein A is as defined hereinbefore,
or with n-butyl vinyl ether under Heck reaction conditions to obtain a trans compound of formula Ib:

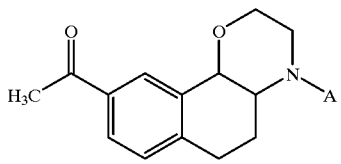

(Ib)

wherein A is as defined hereinbefore, and, optionally, the compound Ia, obtained previously, is treated with a mixture of hydrochloric acid and acetic acid at reflux to obtain a trans compound of formula Ic:

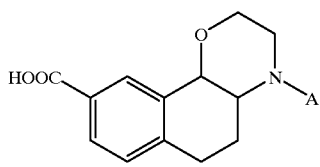

(Ic)

wherein A is as defined hereinbefore,
which compound Ic is optionally treated:
  either with a compound of formula IV:

 $R_3$—OH  (IV)

wherein $R_3$ is as defined hereinbefore,
in the presence of hydrochloric acid, to obtain a trans compound of formula Id:

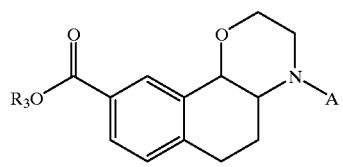

(Id)

wherein A and $R_3$ are as defined hereinbefore,
or with a compound of formula V:

(V)

wherein $R_1$ and $R_2$ are as defined hereinbefore, in the presence of 2-(1H-benzotriazol-1-yl)-1,1,3,3-tetramethyluronium tetrafluoroborate, triethylamine and a catalytic amount of 4-dimethylaminopyridine in methylene chloride, to obtain a trans compound of formula Ie:

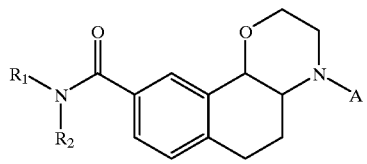

(Ie)

wherein A, $R_1$ and $R_2$ are as defined hereinbefore.

The totality of the trans compounds of formula Ia, Ib, Ic, Id and Ie constitute the totality of the trans compounds of formula I.

The starting materials of formula II were prepared according to processes described in the literature starting from known substances.

The optically active forms of the compounds of formula I were obtained either starting from the optically active forms of the starting materials of formula II, or by splitting the racemic forms of the compounds of formula I, according to methods known from the literature.

The present invention relates also to pharmaceutical compositions comprising as active ingredient a compound of formula I or a physiologically tolerable salt thereof, mixed with or associated with one or more appropriate pharmaceutical excipients.

The pharmaceutical compositions so obtained are generally presented in dosage form containing from 0.5 to 25 mg of active ingredient. They may, for example, be in the form of tablets, dragées, gelatin capsules, suppositories or injectable or drinkable solutions and may be administered by the oral, rectal or parenteral route.

The dosage may vary according to the age and weight of the patient, the administration route, the nature of the disorder and associated treatments, and ranges from 0.5 to 25 mg of active ingredient from 1 to 3 times per day.

The following Examples, which are given as non-limiting examples, illustrate the present invention. The melting points were determined either using a Kofler hot plate (K), or a hot plate under a microscope (MK). The proton nuclear magnetic resonance spectra (NMR) were carried out at 200 MHz unless indicated otherwise.

EXAMPLE 1

Trans-3,4,4a,5,6,10b-hexahydro-9-cyano-4-propyl-2H-naphtho [1,2-b]-1,4-oxazine and its hydrochloride Step A: trans-3,4,4a,5,6,10b-hexahydro-9-[(trifluoromethyl)sulphonyloxy]-4propyl-2H-naphthol [1,2-b]-1,4-oxazine 18.7 ml of triflic anhydride are added slowly to a solution of 21.0 g of trans-3,4,4a,5,6,10b-hexahydro-9-hydroxy-4-propyl-2H-naphtho[1,2-b]-1,4-oxazine in 17 ml of pyridine while maintaining the temperature at from 0° C. to 5° C. After 1 hour's stirring at 0° C., the reaction mixture is concentrated in vacuo. The evaporation residue is chromatographed on a silica column (eluant: $CH_2Cl_2/CH_3COOC_2H_5$; 85/15) to yield 22.4 g of the expected product.

M.p.: 56° C.–57° C. (K)

Yield: 69%

Step B: title compound 2.39 g of $Zn(CN)_2$ and 1.34 g of $Pd[P(C_6H_5)_3]_4$ are added in succession, at room temperature, to a degassed solution of 11.0 g of the title compound of Step A in 55 ml of dimethylformamide (DMF). The reaction mixture is heated for 3 hours at 80° C. 2.39 g of $Zn(CN)_2$ and 1.34 g of $Pd[P(C_6H_5)_3]_4$ are again added thereto in succession at 80° C. After 18 hours' heating at 80° C., the reaction mixture is poured into 500 ml of water. The mixture is extracted with ethyl ether. The organic phases are combined and extracted four times with 1N HCl. The aqueous phases are combined, rendered alkaline with sodium hydroxide solution and extracted with ethyl ether. The organic phases are combined, washed once with brine, dried over magnesium sulphate and concentrated in vacuo to yield 6.27 g of the desired product. 1 g of the product is chromatographed on a silica column (eluant: $CH_2Cl_2/CH_3COOC_2H_5$; 90/10) to yield 0.66 g of the expected base, the hydrochloride of which is crystallised from ethyl acetate.

M.p.: 201–203° C. (MK) (sublimation 190–195° C.)

$^1$H-NMR: 300 MHz $(DMSO)d_6$ 11.6 ppm, m, 1H; 7.75 ppm, d, 1H; 7.7 ppm, dd, 1H; 7.4 ppm, d, 1H; 5.0 ppm, d, 1H; 4.25 ppm, d, 2H; 3.6 ppm, d, 1H; 3.45–3.15 ppm, m, 3H; 3.0 ppm, m, 3H; 2.5 ppm, m, 1H; 1.75 ppm, m, 2H; 0.95 ppm, t, 3H.

EXAMPLE 2

Trans-3,4,4a,5,6,10b-hexahydro-9-carbamoyl-4-propyl-2H-naphtho[1,2-b]-1,4-oxazine A solution of 1 g of the title product of Example 1 in 37 ml of ethanol and 0.6 g of KOH is heated at reflux. After 48 hours, the reaction mixture is concentrated in vacuo. The residue is taken up in 200 ml of a 95:5 $CH_2Cl_2/CH_3OH$ mixture. The solution, washed twice with brine and dried over magnesium sulphate, is concentrated in vacuo to yield 0.8 g of a solid which recrystallises from methanol.

M.p.: 200–202° C. (MK)

Yield: 72%

$^1$H-NMR: $(DMSO)d_6$ 7.94 ppm, s, 1H; 7.90 ppm, s, 1H (exchangeable); 7.66 ppm, dd, 1H; 7.15 ppm, s, 1H (exchangeable); 7.14 ppm, d, 1H; 4.20 ppm, d, 1H; 4.00 ppm, dd, 1H; 3.78 ppm, m, 1H; 2.98–2.70 ppm, m, 4H; 2.40–2.0 ppm, m, 4H; 1.60–1.35 ppm, m, 3H; 0.9 ppm, t, 3H.

EXAMPLE 3

(+)-Trans-3,4,4a,5,6,10b-hexahydro-9-carbamoyl-4-propyl-2H-naphtho[1,2-b]-1,4-oxazine 2 g of the title product of Example 2 are chromatographed by normal phase high-pressure chromatography on a chiral support (Chiracel AD®, eluant: ethanol 100%, flow rate: 5 ml/min, detection 240 nm) to yield 0.72 g of the least retained enantiomer. Recrystallisation from methanol yields 0.7 g of the title product (ee>99%).

M.p.: 200–202° C. (MK)

$^1$H-NMR: $(DMSO)d_6$ 7.94 ppm, s, 1H; 7.90 ppm, s, 1H (exchangeable); 7.66 ppm, dd, 1H; 7.15 ppm, s, 1H (exchangeable); 7.14 ppm, d, 1H; 4.20 ppm, d, 1H; 4.00 ppm, dd, 1H; 3.78 ppm, m, 1H; 2.98–2.70 ppm, m, 4H; 2.40–2.0 ppm, m, 4H; 1.60–1.35 ppm, m, 3H; 0.9 ppm, t, 3H.

$[\alpha]^{20°\ C.}$: (c=1%, $CHCl_3$).

| λ nm | 589 | 578 | 546 | 436 | 365 |
| --- | --- | --- | --- | --- | --- |
| α° | +65.8 | +68.5 | +78.0 | +131.2. | +200.0 |

EXAMPLE 4

(−)-Trans-3,4,4a,5,6,10b-hexahydro-9-carbamoyl-4-propyl-2H-naphthol[1,2-b]-1,4-oxazine 2 g of the title product of Example 2 are chromatographed by normal phase high-pressure chromatography on a chiral support (Chiracel AD®, eluant: ethanol 100%, flow rate: 5 ml/min, detection 240 nm) to yield 0.71 g of the most retained enantiomer. Recrystallisation from methanol yields 0.69 g of the title product (ee>99%).

M.p.: 200–202° C. (MK)

$^1$H-NMR: $(DMSO)d_6$ 7.94 ppm, s, 1H; 7.90 ppm, s, 1H (exchangeable); 7.66 ppm, dd, 1H; 7.15 ppm, s, 1H (exchangeable); 7.14 ppm, d, 1H; 4.20 ppm, d, 1H; 4.00 ppm, dd, 1H; 3.78 ppm, m, 1H; 2.98–2.70 ppm, m, 4H; 2.40–2.0 ppm, m, 4H; 1.60–1.35 ppm, m, 3H; 0.9 ppm, t, 3H.

$[\alpha]^{20°\ C.}$: (c=1%, $CHCl_3$).

| λ nm | 589 | 578 | 546 | 436 | 365 |
| --- | --- | --- | --- | --- | --- |
| α° | −65.4 | −68.3 | −77.6 | −131.2 | −197.6 |

EXAMPLE 5

Trans-3,4,4a,5,6,10b-hexahydro-9-(N-methylcarbamoyl)-4-propyl-2H-naphthol [1,2-b]-1,4-oxazine Step A: trans-3,4,4a,5,6,10b-hexahydro-4-propyl-2H-naphthol[1,2-b]-1,4-oxazine-9-carboxylic acid hydrochloride 68 ml of 36% hydrochloric acid are added at room temperature to a solution of 6.14 g of the title compound of Example 1 in 68 ml of glacial acetic acid. After 18 hours at reflux, the reaction mixture is brought to dryness. The solid residue is triturated in ethyl ether, filtered and dried to yield 8.65 g of a white powder which is recrystallised from 80 ml of water. 6.9 g of the desired product are obtained.

M.p.: 260° C. (K)

Yield: 89%

Step B: title compound of the Example

Monomethylamine is introduced in the course of one hour, at room temperature, into a solution of 1 g of the compound obtained above, 1.13 g of 2-(1H-benzotriazol-1-yl)-1,1,3,3-tetramethyluronium tetrafluoroborate (TBTU) and 1.1 ml of triethylamine in 14 ml of methylene chloride. After 18 hours' stirring at room temperature, the reaction mixture is diluted with methylene chloride, washed once with 1N NaOH and three times with $H_2O$, dried over magnesium sulphate and then concentrated in vacuo. The solid residue (1.14 g) is recrystallised from 100 ml of ethyl acetate to yield 0.41 g of the title compound.

M.p.: 179–180° C.

Yield: 44%

$^1$H-NMR: 300 MHz $(CDCl_3)$ 7.8 ppm, s, 1H; 7.7 ppm, d, 1H; 7.1 ppm, d, 1H; 6.2 ppm, m, 1H (exchangeable); 4.3 ppm, d, 1H; 4.1–3.9 ppm, m, 2H; 2.98 ppm, s, 3H; 2.9 ppm, m, 2H; 2.9 ppm, m, 1H; 2.8–2.45 ppm, m, 2H; 2.3 ppm, m, 2H; 2.3–1.6 ppm, m, 2H; 1.5 ppm, m, 2H; 0.9 ppm, t, 3H.

EXAMPLE 6

Trans-3,4,4a,5,6,10b-hexahydro-9-(N,N-dimethylcarbamoyl)-4-propyl-2H-naphtho [1,2-b]-1,4-oxazine 1 g of the product obtained in Example 5, Step A is treated as described in Example 5, Step B (using dimethylamine instead of monomethylamine) to yield 0.46 g of the title product after solidifying in isopropyl ether.

M.p.: 85–87° C. (MK)

Yield: 47%

$^1$H-NMR: 300 MHz (CDCl$_3$) 7.6 ppm, s, 1H; 7.2 ppm, d, 1H; 7.1 ppm, d, 1H; 4.30 ppm, d, 1H; 4.1–3.9 ppm, m, 2H; 3.05 ppm, s 6H; 2.9 ppm, m, 2H; 2.9 ppm, m, 1H; 2.8–2.5 ppm, m, 2H; 2.2 ppm, m, 2H; 2.3–1.5 ppm, m, 2H; 1.5 ppm, m, 2H; 0.9 ppm, t, 3H.

EXAMPLE 7

Trans-3,4,4a,5,6,10b-hexahydro-9-(N-butylcarbamoyl)-4-propyl-2H-naphtho [1,2-b]-1,4-oxazine At room temperature, 1 g of the product obtained in Example 5, Step A, 1.13 g of TBTU and 0.26 g of n-butylamine are suspended in 14 ml of methylene chloride. 1.1 ml of triethylamine are added at room temperature and the reaction mixture is stirred for 18 hours at that temperature. The reaction mixture is diluted with methylene chloride, washed once with 1N NaOH and three times with H$_2$O, dried over magnesium sulphate and then concentrated in vacuo. The oily residue is solidified in isopropyl ether to yield 0.6 g of the title product.

M.p.: 128–131° C. (MK)

Yield: 56%

$^1$H-NMR: 300 MHz (CDCl$_3$) 7.8 ppm, s, 1H; 7.7 ppm, d, 1H; 7.15 ppm, d, 1H; 6.15 ppm, t, 1H (exchangeable); 4.1–3.95 ppm, m, 2H; 3.4 ppm, q, 2H; 3.0 ppm, m, 2H; 2.9 ppm, m, 1H; 2.85–2.5 ppm, m, 2H; 2.3 ppm, m, 2H; 2.3–1.6 ppm, m, 2H; 1.6–1.4 ppm, m, 6H; 0.9 ppm, t, 3H.

EXAMPLE 8

Trans-3,4,4a,5,6,10b-hexahydro-9-(N-p-methoxyphenylcarbamoyl)-4-propyl-2H-naphtho[1,2-b]-1,4-oxazine At room temperature, 0.8 g of the product obtained in Example 5, Step A, 0.9 g of TBTU, a catalytic amount of 4-dimethylaminopyridine and 0.35 g of p-methoxyaniline are suspended in 11 ml of methylene chloride. 0.9 ml of triethylamine is added at room temperature and the reaction mixture is stirred for 18 hours at that temperature. The reaction mixture is diluted with methylene chloride, washed once with 1N NaOH and three times with H$_2$O, dried over magnesium sulphate and then concentrated in vacuo. The solid residue is recrystallised from ethyl acetate to yield 0.42 g of the title product.

M.p.: 185–186° C. (MK)

Yield: 43%

$^1$H-NMR: 300 MHz (CDCl$_3$) 7.92 ppm, s, 1H; 7.85 ppm, d, 1H; 7.8 ppm, m, 1H (exchangeable); 7.5 ppm, d, 2H; 7.2 ppm, d, 1H; 6.9 ppm, d, 2H; 4.3 ppm, d, 1H; 4.1–3.45 ppm, m, 2H; 3.8 ppm, s, 3H; 2.95 ppm, m, 1H; 2.9 ppm, m, 2H; 2.8–2.5 ppm, m, 2H; 2.3 ppm, m, 2H; 2.3–1.6 ppm, m, 2H; 1.6 ppm, m, 2H; 0.9 ppm, t, 3H.

EXAMPLE 9

Trans-3,4,4a,5,6,10b-hexahydro-9-(N-p-methoxybenzylcarbamoyl)-4-propyl-2H-naphtho[1,2-b]-1,4-oxazine 0.7 g of the product obtained in Example 5, Step A is treated as described in Example 7 (using p-methoxybenzylamine instead of n-butylamine) to yield 0.34 g of the title product after recrystallisation from ethyl acetate.

M.p.: 148–150C. (MK)

Yield: 38%

$^1$H-NMR: 300 MHz (CDCl$_3$) 7.85 ppm, d, 1H; 7.75 ppm, dd, 1H; 7.3 ppm, d, 2H; 7.2 ppm, d, 1H; 6.9 ppm, d, 2H; 6.4 ppm, t, 1H (exchangeable); 4.6 ppm, m, 2H; 4.3 ppm, d, 1H; 4.1–3.95 ppm, m, 2H, 3.8 ppm, s, 3H; 2.9 ppm, m, 4H; 2.3 ppm, m, 4H; 1.5 ppm, m, 3H; 0.9 ppm, t, 3H.

EXAMPLE 10

Trans-3,4,4a,5,6,10b-hexahydro-9-ethoxycarbonyl-4-propyl-2H-naphtho [1,2-b]-1,4-oxazine and its hydrochloride 1 g of the title compound of Example 1 is dissolved in a mixture of 15 ml of chloroform and 15 ml of ethanol. The solution is cooled to 0° C. and a stream of gaseous HCl is introduced bubble by bubble for 1 hour. The mixture is brought to room temperature and stirred for 24 hours. The mixture is then concentrated in vacuo, taken up in 100 ml of phosphate buffer and stirred for 3 days at room temperature. The solution is rendered basic with 1N sodium hydroxide solution and extracted with methylene chloride. Evaporation yields 1 g of the title product, which is converted into its hydrochloride by a 4N solution of ethereal hydrogen chloride. Weight : 1.05 g.

M.P.: 220–221° C. (MK)

Yield: 79%

$^1$H-NMR: 300 MHz (CDCl$_3$) 13.20 ppm, large s., 1H (exchangeable); 8.18 ppm, s, 1H; 7.92 ppm, dd, 1H; 7.18 ppm, d, 1H; 8.35 ppm, d, 1H; 4.70 ppm, d, 1H; 4.38 ppm, q, 2H; 4.22 ppm, dd, 1H; 3.55 ppm, d, 1H; 3.33 ppm, td, 1H; 3.00 ppm, m, 5H; 2.57 ppm, m, 1H; 2.40 ppm, m, 1H; 2.02 ppm, m, 1H; 1.80 ppm, m, 1H; 1.40 ppm, t, 3H; 1.05 ppm, t, 3H.

EXAMPLE 11

Trans-3,4,4a,5,6,10b-hexahydro-9-acetyl-4-propyl-2H-naphthol[1,2-b]-1,4-oxazine and its hydrochloride 1.3 g of the compound obtained in Step A of Example 1 is dissolved in 10 ml of DMF. At room temperature, 0.57 ml of triethylamine, 2.22 ml of n-butyl vinyl ether, 42 mg of 1,3-bis-(diphenylphosphino)propane and 19.3 mg of

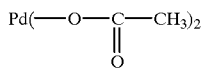

are added.

The solution is heated for 3 hours at 80–90° C. then, after returning to room temperature, 15 ml of 1N HCl are added. Stirring is continued for 1 hour. The reaction mixture is then diluted with 1N HCl and the solution is washed several times with ether. The aqueous phase is rendered alkaline with sodium hydroxide solution and extracted four times with methylene chloride. Evaporation and purification by flash chromatography ($CH_2Cl_2/CH_3COOC_2H_5$: 90/10 and 80/20) yields 0.61 g of the expected product, the hydrochloride of which is prepared by the action of ethereal hydrogen chloride. Weight: 0.57 g.

M.p.: 225–226° C. (MK)

Yield: 54%

$^1$H-NMR: 300 MHz (DMSO) 11.58 ppm, s, 1H (exchangeable); 8.03 ppm, s, 1H, 7.88 ppm, d, 1H; 7.33 ppm, d, 1H, 5.01 ppm, d, 1H; 4.22 ppm, d, 2H; 3.58 ppm, d, 1H; 3.40 to 3.20 ppm, m, 4H; 3.15 to 2.90 ppm, m, 3H; 2.55 ppm, s, 3H; 2.04 ppm, m, 1H; 1.72 ppm, m, 2H; 0.98 ppm, t, 3H.

EXAMPLE 12

Pharmacological Study

A. In vitro: human $D_2$ and $D_3$ receptor binding study

Cell Culture

CHO (Chinese Hamster Ovary) cells are transfected in a stable manner with the gene encoding the human dopamine $D_2$ or $D_3$ receptor in accordance with methods known from the literature. The native cells are deficient in the enzyme DHFR (DiHydroFolate Reductase). The cells are cultured in an incubator at 37° C. in a humid atmosphere of 5% $CO_2$, 95% air. The transfections are carried out using Lipofectin (Gibco). The CHO cells co-transfected with the human $D_2$ receptor and the phleomycin resistance gene are selected for their resistance to the presence of that antibiotic in the culture medium. The cells transfected with the human $D_3$ receptor are selected in the presence of methotrexate in a medium containing no hypoxanthine/thymidine. The compositions of the culture media used are: for CHO-$D_2$: DMEM (Dulbecco's Modified Eagle Medium) supplemented with 10% foetal calf serum and hypoxanthine/thymidine; and for CHO-$D_3$: DMEM supplemented with 10% dialysed foetal calf serum. The cells are harvested at confluence and the membranes are then prepared.

Membrane Preparation

After a few minutes in the presence of 0.2% trypsin, the cells are recovered and centrifuged at 2,000 g for 5 minutes. The cell mass, which is re-suspended in 10 mM Tris-HCl buffer, pH 7.5, containing 5 mM $MgSO_4$, is then passed over Polytron®. The homogenate is then centrifuged at 50,000 g for 15 minutes, and the mass is re-suspended by gentle sonication in an incubation buffer of the following composition: 50 mM Tris-HCl, pH 7.5, containing 120 mM NaCl, 5 mM KCl, 2 mM $CaCl_2$, 5 mM $MgCl_2$. The membranes are then divided into aliquots and stored at −80° C. until the day of the experiment.

Binding Experiments

Incubation is carried out in polypropylene tubes at a final volume of 400 µl containing:
- 100 µl of [$^{125}$I]-iodosulpride (Amersham) at 0.1 and 0.2 nM for the $D_2$ and $D_3$ receptors, respectively
- 100 µl of buffer (total tubes)
- or 100 µl of 10 µM raclopride (non-specific binding)
- or 100 µl of compound
- 200 µl of membrane preparation containing the $D_2$ or $D_3$ receptors in a buffer to which
- 0.2% BSA (bovine serum albumin) has been added.

The ranges of concentration of each compound include at least seven points determined in triplicate, each experiment being repeated at least twice.

The incubation, which lasts for thirty minutes at 30° C., is terminated by means of rapid filtration over a Brandle apparatus, followed by three consecutive rinses with Tris-HCl buffer, pH 7.4, containing 120 mM NaCl. The recovered filters are then counted using a gamma counter.

Analysis of the Results

The $IC_{50}$, which represents the concentration that inhibits the binding of the radioligand by 50%, is calculated by non-linear regression (Prism Graph method).

The $K_i$ value is derived from the formula $K_i = IC_{50}/(1+L/Kd)$ where L is the concentration of [$^{125}$I]-iodosulpride used in the experiment and Kd is its dissociation constant. The results are expressed in the form of $pK_i$ ($pK_i = -\log K_i$).

For the human $D_2$ and $D_3$ receptors, the Kd are, respectively, 0.5 and 1.31 nM.

Results

By way of example, the product of Example 3 has a $pK_i$ of 8 for the $D_3$ receptor and of 6.5 for the $D_2$ receptor.

B. In vivo

1. Test recording the unitary extracellular electrical activity in the ventral tegmentum area of the rat Principle The administration of a dopaminergic agonist decreases the discharge frequency of neurons in a dose-dependent manner. That effect is reversed by haloperidol, a dopaminergic antagonist.

Method

The rats are anaesthetised with chloral hydrate (400 mg/kg, i.p.) and placed in a stereotactic apparatus (Unimécanique, France) after catheterisation of the femoral vein. The level of anaesthesia is maintained by i.p. administration of chloral hydrate every hour; the rectal temperature is maintained at 37±1° C. by means of a thermostatically controlled heated cover. A tungsten microelectrode (10 MΩ, 1 µm) is inserted using an electronic microinsertion device (Unimécanique, France) into the ventral tegmentum area (AP: −5.5/bregma; L: 0.7; H: 7.0–8.5/dura; Paxinos and Watson atlas, 1986). The potentials of the dopaminergic cells are recognised by their morphology (triphasic potentials+/−/+, of a duration greater than 3 msec), their discharge rhythm, whether regular or in bursts of decreasing amplitude, and their discharge frequency, which is from 2 to 8 Hz. A single cell per animal is used for the recording.

After a period ≧5 min. (basal activity) and a first injection of carrier (distilled water to which a few drops of dilute lactic acid have been added; pH adjusted to 5 with 1N NaOH), the products of the invention are administered intravenously in cumulatively increasing doses at intervals of 2–3 min..

Analyses of the Results

Acquisition of the data is effected by the software Spike2 (Cambridge Electronic Design, England). The discharge frequency is measured over one minute at the maximum variation between each injection and is expressed as a percentage variation in relation to the basal activity (average of the 5 minutes preceding the first treatment) defined as 100%. The effect of the products is evaluated statistically by a variance analysis over repeated measurements, followed by a Newman-Keuls test for comparing the effects of different doses with the effect of the carrier.

Results

By way of example, the Table which follows shows the effects of the product of Example 3.

| Doses μg/kg i.v. | 0 | 0.5 | 1 | 2 | 4 | 8 | haloperidol 16 μg/kg i.v. |
|---|---|---|---|---|---|---|---|
| Example 3 | 97.2 ± 2.05 | 80.4 ± 5.54 | 56.6 ± 11.4* | 25.0 ± 8.68* | 1.56 ± 1.12* | 0.00* | 110.5 ± 14.9 |

Individual values (n = 4) = mean ± standard error of the mean.
Comparison of the effects of different doses of the compound by variance analysis of repeated measurements:
Example 3, F(6.18) = 28.29, p < 0.001. Newman-Keuls test. * = p ≤ 0.05.

2. Ultrasonic vocalisation test in the rat

Principle

When a rat is placed in an environment previously associated with an unpleasant experience (electric shocks to the paws), its anxiety is shown by the emission of inaudible cries (or ultrasonic vocalisations). The anxiolytic activity of a product is demonstrated by a reduction in the duration of those vocalisations.

Apparatus

Standard cages (Coulbourn Instruments), placed in sound-absorbing ventilated boxes, are fitted with a floor composed of electrifiable metal bars (shock generator and scrambler Med Associates Inc) and with a microphone located in the centre of the ceiling. The ultrasounds are converted into an audible range (bat-detector Buitenbedrijf). The signals modified in that way are filtered and then processed (RTS software, Engineering Design). The spectrograms obtained are recorded on DAT tapes.

Method

Male Wistar rats, weighing 180–200 g on arrival, are placed in cages of four with free access to water and food from five days before the beginning of the study until the end of the study. The procedure employed is divided into three successive stages separated by 24 hours, called training, selection and test. During the training period, the animals are placed individually into cages where they receive six electric shocks (0.8 mA, 8 s) randomly distributed over a period of seven minutes. Selection comprises placing each animal in a cage for two minutes where they receive a single shock and putting them back in the cage thirty minutes later to record the ultrasonic vocalisations for a period of ten minutes; those animals where the duration of the vocalisations is less than 90 seconds are excluded from the remainder of the experiment. The test phase proceeds in a similar manner to the selection stage, except that the products or the carrier are administered at the end of the two-minute period.

Results

By way of example, the Table which follows shows the effects of the product of Example 3 administered subcutaneously in a volume of 1 ml/kg

| dose mg/kg s.c. | duration of the ultrasonic vocalisations (s) mean ± s.e.m. (n) Example 3 |
|---|---|
| 0 | 251 ± 29 (16) |
| 0.0025 | 163 ± 54 (7) |
| 0.01 | 144 ± 79 (5) |

-continued

| dose mg/kg s.c. | duration of the ultrasonic vocalisations (s) mean ± s.e.m. (n) Example 3 |
|---|---|
| 0.04 | 17 ± 13 (6)** |
| 0.16 | 0.3 ± 0.3 (4)** | s.e.m.: standard error of the mean
n: number of rats
comparison versus carrier (Dunnett test): **p < 0.01

At doses of 0.04 and 0.16 mg/kg, that product causes a large reduction in the duration of the vocalisations, indicating its anxiolytic activity.

3. Forced swimming test

Principle

The forced swimming test (Porsolt R. et al, Eur. J. Pharmacol., 1978, 47, 379–91) is a behavioural test which comprises inducing a state of despair in the rat by placing the naive animal in an enclosure full of water, from which it cannot escape, for a period of fifteen minutes. For the first five to ten minutes the rat struggles vigorously, but finally adopts an immobile posture during the last part of the test. Placed in the same enclosure the next day, the animal remains immobile for the majority of the test (5 minutes' duration). The anti-depressants reduce the duration of immobility of the rat during the test.

Procedure

The experiment is carried out over two days, with a 24-hour interval, on rats of an average weight of 170 g, housed the day before in individual cages, with free access to food and drink.

On the first day, each rat is placed for fifteen minutes in a glass cylinder (20 cm diameter ×40 cm high) filled to a height of 15 cm with water maintained at 25° C. On the second day, the animal is placed in a cylinder again for a period of five minutes; the total period of immobility (in seconds) of the rat is measured. The product or solvent is administered to the animal thirty minutes before the beginning of the test.

Results

By way of example, and to illustrate the activity of the products of the invention, the effects of the product of Example 3 are recorded in the following Table.

| product | dose mg/kg s.c. | immobility (sec) mean ± s.e.m. (n) |
|---|---|---|
| Controls (distilled water) | 0 | 172.2 ± 19.87 (8) |
| Example 3 | 0.04 | 183.14 ± 4.06 (5) |
|  | 0.16 | 170.71 ± 23.09 (5) |
|  | 0.31 | 130.33 ± 18.67 (5) |
|  | 0.63 | 36.87 ± 22.28* (5) |
|  | 10.0 | 0.27 ± 0.27* (5) |

(n) = number of rats

The product of Example 3 reduces the period of immobility of the animal in a dose-dependent manner, and thus presents an excellent anti-depressant effect with an $ID_{50}$ of 0.41 mg/kg s.c.

4. "Rotations" induced by dopaminergic agonists in rats having a unilateral lesion of the Substantia nigra Principle The unilateral injection of the neurotoxin 6-hydroxy-dopamine (6-OH-DA) into the *Substantia nigra* causes degeneration of the ascending nigrostriated pathways, with hypersensitivity of the post-synaptic dopaminergic receptors on the side of the lesion. In a rat subjected to such a lesion, the systemic administration of direct agonist products (apomorphine) induces contralateral rotations (on the side opposite to the lesion). This test makes it possible to demonstrate the agonistic dopaminergic properties of products directed therapeutically at Parkinson's disease.

Methods

Lesion: the lesion is made in male Wistar rats weighing from 280 to 330 g that are anaesthetised with pentobarbital (40–50 mg/kg i.p.) and that have received a dose of 25 mg/kg i.p. of desipramine. The animal is placed in a KOPF stereotactic apparatus, with the cranium oriented in accordance with the Pellegrino and Cushman Atlas (1979). A volume of 4 μl of a solution of 6-OH-DA (2 μg/μl) is slowly injected, using a microperfuser, at the level of the left *Substantia nigra* (A=2,4 mm; L=2.0 mm; V=3.1 mm, in relation to the interaural zero) (U. Ungerstedt, *Acta Physiol. Scandi. Suppl.*, 1971, 367, 69–93).

Apparatus: The recording of the number and direction of the rotations is carried out automatically by computer using the ROTACOUNT system (Columbus Co, USA). The animal is placed in a flat-bottomed cylinder 30 cm in diameter and 50 cm in height. A fine semi-rigid cable encircles the animal below the front paws and is connected to an optical counting cell which is located above the cylinder and connected to the computer.

Selection of the lesioned animals: one month after inducing the lesion with 6-OH-DA, the correctly lesioned animals are selected in accordance with a criterion of at least 150 contralateral rotations performed in the course of 1 hour after administration of the dopaminergic agonist apomorphine (0.04 mg/kg, s.c.).

Procedure: the animals are tested once per week, the products of the invention being administered in alternation with the dopaminergic agonist. Recording of the contralateral rotations commences with the injection of the dopaminergic agonist (T0) and lasts for one hour. Each animal is its own control.

Results

By way of example, the following Table shows the effects of the product of Example 3 administered s.c..

| product | dose mg/kg s.c. | contralateral rotations mean ± s.e.m. (n) |
|---|---|---|
| Serum control | 0 | 11.0 ± 14.3 (23) |
| Apomorphine control | 0.04 | 531.0 ± 54.1 (14) |
| Example 3 | 0.01 | 84.5 ± 79.7 (2) |
|  | 0.04 | 223.0 ± 103.5 (6) |
|  | 0.16 | 336.6 ± 85.5 (7) |

(n) = number of rats

The product of Example 3 is active in this test from a dose of 0.04 mg/kg.

We claim:

1. A compound selected from those of formula I:

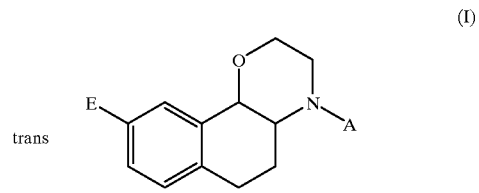

(I)

trans wherein:

A represents: $(C_1-C_{10})$alkyl, $(C_3-C_{10})$alkenyl, or $(C_3-C_{10})$alkynyl, each of which is straight-chain or branched and optionally substituted by one or more $(C_3-C_8)$ cycloalkyl, or by aryl selected from the group consisting of: phenyl, thienyl, and pyridyl, each of which is unsubstituted or substituted by one or more substituents selected from the group consisting of: halogen, hydroxy, and straight-chain or branched $(C_1-C_6)$ -alkyl or -alkoxy, E represents:

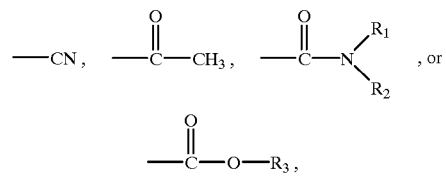

wherein:

$R_1$ and $R_2$, which may be identical or different, each represents hydrogen or has the meaning given for A above, and $R_3$ represents hydrogen or straight-chain or branched $(C_1-C_5)$ alkyl;

in racemic form or in the form of optical isomers, and an addition salt thereof with a pharmaceutically acceptable acid.

2. A compound of claim 1 which is selected from trans-3,4,4a,5,6,10b-hexahydro-9-cyano-4-propyl-2H-naphtho[1,2-b]-1,4-oxazine and its hydrochloride.

3. A compound of claim 1 which is trans-3,4,4a,5,6,10b-hexahydro-9-carbamoyl-4-propyl-2H-naphtho[1,2-b]-1,4-oxazine.

4. A compound of claim 1 which is (+)-trans-3,4,4a,5,6,10b-hexahydro-9-carbamoyl-4-propyl-2H-naphtho[1,2-b]-1,4-oxazine.

5. A method for treating a living animal body afflicted with a condition selected anxiety, and depression, comprising the step of administering to the said living animal body an amount of a compound of claim 1 which is effective for alleviation of said condition.

6. A pharmaceutical composition, comprising as active ingredient a compound according to claim 1 together with one or more pharmaceutically-acceptable excipients or vehicles.

7. A pharmaceutical composition, comprising as active ingredient a compound according to claim 2 together with one or more pharmaceutically-acceptable excipients or vehicles.

8. A pharmaceutical composition, comprising as active ingredient a compound according to claim 3 together with one or more pharmaceutically-acceptable excipients or vehicles.

9. A pharmaceutical composition, comprising as active ingredient a compound according to claim 4 together with one or more pharmaceutically-acceptable excipients or vehicles.

* * * * *

UNITED STATES PATENT AND TRADEMARK OFFICE
CERTIFICATE OF CORRECTION

PATENT NO. : 6,025,356
DATED : Feb. 15, 2000
INVENTOR(S) : J-L Peglion, J-C Harmange, M. Millan, F. Lejeune It is certified that error appears in the above-identified patent and that said Letters Patent is hereby corrected as shown below:

Column 4, line 35: "drag ees," should be one word -- dragées, --.

Column 6, line 13(approx.): "propyl-2H-naphthol" should read -- propyl-2H-naphtho --.

Column 6, line 38(approx.): "-2H-naphthol" should read -- 2H-naphtho --.

Column 8, line 25: "4.1-3.95 ppm,m,2H," should read -- 4.1-3.95 ppm,m,2H; --.

Column 8, line 61: "naphthol" should read -- naphtho --.

Column 9, line 22: "8.03 ppm,s,1H," should read -- 8.03 ppm,s,1H; --.

Column 9, line 23: At the beginning of the line, "ppm,d,1H," should read -- ppm,d,1H; --.

Column 9, line 67: This line should be moved to the top of column 10.

Column 11, line 67: This line should be moved to the top of column 12.

Column 14, line 12(approx.): "11.0± 14.3(23)" should read -- 11.0 ± 4.3 (23) --.

UNITED STATES PATENT AND TRADEMARK OFFICE
CERTIFICATE OF CORRECTION

PATENT NO. : 6,025,356
DATED : Feb. 15, 2000
INVENTOR(S) : J-L Peglion, J-C Harmange, M. Millan, F. Lejeune It is certified that error appears in the above-identified patent and that said Letters Patent is hereby corrected as shown below:

Column 14, line 60: Insert a -- - -- (hyphen) between the words "pharmaceutically" and "acceptable".

Column 15, line 6: Insert the word -- from -- between "selected" and "anxiety".

Signed and Sealed this

Twenty-third Day of January, 2001

Attest:

Q. TODD DICKINSON

*Attesting Officer*     *Commissioner of Patents and Trademarks*